(12) United States Patent
Moriyama

(10) Patent No.: US 8,465,419 B2
(45) Date of Patent: Jun. 18, 2013

(54) ENDOSCOPE INSERTION UNIT, ENDOSCOPE AND ENDOSCOPE SYSTEM

(75) Inventor: Hiroki Moriyama, Akishima (JP)

(73) Assignee: Olympus Corporation, Tokyo (JP)

( * ) Notice: Subject to any disclaimer, the term of this patent is extended or adjusted under 35 U.S.C. 154(b) by 974 days.

(21) Appl. No.: 11/642,557

(22) Filed: Dec. 20, 2006

(65) Prior Publication Data

US 2007/0106118 A1    May 10, 2007

Related U.S. Application Data

(63) Continuation of application No. PCT/JP2005/011542, filed on Jun. 23, 2005.

(30) Foreign Application Priority Data

Jul. 1, 2004    (JP) .................................. 2004-196062

(51) Int. Cl.
*A61B 1/00*    (2006.01)
*A61B 1/04*    (2006.01)

(52) U.S. Cl.
USPC ............ 600/127; 600/114; 600/128; 600/129

(58) Field of Classification Search
USPC ......... 600/114–116, 139, 105, 130, 127–129, 600/104; 604/101.01, 101.05
See application file for complete search history.

(56) References Cited

U.S. PATENT DOCUMENTS

| | | | | |
|---|---|---|---|---|
| 4,588,398 A | * | 5/1986 | Daugherty et al. | 604/265 |
| 5,002,558 A | * | 3/1991 | Klein et al. | 606/192 |
| 5,031,603 A | * | 7/1991 | Gautier et al. | 600/135 |
| 5,078,681 A | * | 1/1992 | Kawashima | 606/198 |
| 5,083,549 A | | 1/1992 | Cho et al. | |
| 5,779,697 A | * | 7/1998 | Glowa et al. | 606/185 |
| 5,941,815 A | * | 8/1999 | Chang | 600/114 |
| 6,234,958 B1 | * | 5/2001 | Snoke et al. | 600/114 |
| 6,503,192 B1 | | 1/2003 | Ouchi | |
| 6,814,697 B2 | * | 11/2004 | Ouchi | 600/121 |

(Continued)

FOREIGN PATENT DOCUMENTS

| | | |
|---|---|---|
| JP | 56-148332 | 11/1981 |
| JP | 2-139603 | 11/1990 |

(Continued)

OTHER PUBLICATIONS

Japanese Office Action dated Apr. 13, 2010.

(Continued)

*Primary Examiner* — Alireza Nia
(74) *Attorney, Agent, or Firm* — Scully, Scott, Murphy & Presser, P.C.

(57)    ABSTRACT

The present invention is an endoscope system comprising an endoscope provided with a distal end inserted into a subject body and a proximal end having a site capable of being held by a physician and provided with an endoscope insertion unit having a first flexible portion arranged on the distal end thereof and a second flexible portion coupled to the proximal end of the first flexible portion and provided with a site having an outer diameter larger than a site having the maximum outer diameter of the first flexible portion; and an endoscope insertion assisting device, in which the inner diameter of a distal opening of an insertion hole through which the endoscope insertion unit is inserted is substantially equal to the outer diameter of the second flexible portion.

12 Claims, 3 Drawing Sheets

U.S. PATENT DOCUMENTS

| | | |
|---|---|---|
| 6,852,078 B2 * | 2/2005 | Ouchi .......................... 600/139 |
| 6,960,162 B2 * | 11/2005 | Saadat et al. ................. 600/114 |
| 2002/0161281 A1 | 10/2002 | Jaffe et al. |
| 2003/0045778 A1 | 3/2003 | Ohline et al. |
| 2004/0080613 A1 | 4/2004 | Moriyama |

FOREIGN PATENT DOCUMENTS

| | | |
|---|---|---|
| JP | 03-073126 | 3/1991 |
| JP | 06-038923 A | 2/1994 |
| JP | 06-070879 | 3/1994 |
| JP | 8-547 | 1/1996 |
| JP | 2001-190494 | 7/2001 |
| JP | 2002-186579 A | 7/2002 |
| JP | 2002-209835 A | 7/2002 |
| JP | 2002-369791 | 12/2002 |
| JP | 2004-141492 | 5/2004 |
| WO | WO 95/24149 | 9/1995 |
| WO | WO 2004/037075 A1 | 5/2004 |

OTHER PUBLICATIONS

Japanese Official Action dated Nov. 30, 2010.

* cited by examiner

ENDOSCOPE INSERTION UNIT, ENDOSCOPE AND ENDOSCOPE SYSTEM

CROSS REFERENCE TO RELATED APPLICATION

This application is a continuation application of PCT/JP 2005/011542 filed on Jun. 23, 2005 and claims benefit of Japanese Application No. 2004-196062 filed in Japan on Jul. 1, 2004, the entire contents of which are incorporated herein by this reference.

BACKGROUND OF THE INVENTION

1. Field of the Invention

The present invention relates to an endoscope insertion unit inserted into a body cavity, an endoscope, and an endoscope system.

2. Description of the Related Art

Endoscopes have come to be widely used in recent years which have an image capturing unit composed of, for example, an object optical system, solid-state image capturing device and circuit board on a distal end of an endoscope insertion unit. The use of this type of endoscope enables a physician to perform various procedures such as observation and treatment of internal organs.

In the case of inserting this type of endoscope into a body cavity, it may be difficult for the physician to insert the endoscope into the body cavity due to an action which tends to contract the body cavity. It is particularly difficult to insert an endoscope insertion unit into a curved portion of a body cavity, such as the sigmoid colon of the large intestine.

The endoscope insertion unit preferably has lower flexibility on the proximal side than the distal side in order to enhance the ease of inserting the insertion unit into a curved portion of a body such as the sigmoid colon of the large intestine. In other words, having higher flexibility for the flexible portion on the distal end of the endoscope insertion unit than the flexibility for the flexible portion on the proximal end makes it easer for the insertion unit to follow the curvature of a curved portion, thereby improving the ease of insertion into a curved portion such as the sigmoid colon.

Consequently, after the distal end of the flexible portion of an endoscope insertion unit has passed a curved section such as the sigmoid colon, the lower the flexibility of the proximal end of the flexible portion of the insertion unit, the less susceptibility to the effect of the force which tends to contract the large intestine. Thus, a physician is able to insert the endoscope insertion unit into the large intestine while smoothly pushing the insertion unit into deeper sections of the large intestine.

Therefore, an endoscope is disclosed in, for example, Japanese Patent Application Laid-open No. 2001-190494, in which, by forming the wall thickness of the outer sheath of a flexible tube of an endoscope to gradually become thicker moving from the distal end to the proximal end, a portion of the flexible tube closer to the proximal end has lower flexibility than the portion closer to the distal end.

In addition, there is a technology for facilitating insertion of an endoscope into a curved section such as the sigmoid colon by using an endoscope insertion assisting device in the form of a so-called endoscope overtube. By inserting this endoscope overtube into a body cavity together with an endoscope, for example, an insertion path for the endoscope is secured within the body cavity, thereby facilitating subsequent insertion and removal of the endoscope. An endoscope system using this type of endoscope overtube is described in, for example, Japanese Patent Application Laid-open No. 2002-369791.

SUMMARY OF THE INVENTION

An endoscope insertion unit of the present invention is provided with a distal end which is inserted into a subject body, and a proximal end having a site capable of being held by a physician; and, is equipped with a first flexible portion arranged on the distal end, and a second flexible portion coupled to the proximal end of the first flexible portion and provided with a site having an outer diameter larger than a site having the maximum outer diameter of the first flexible portion.

An endoscope of the present invention has an insertion unit extending from a control unit which is inserted into a body cavity, and is provided with a substantially tube-shaped first flexible portion on the distal end of the insertion unit, and a substantially tube-shaped second flexible portion on the proximal end of the insertion unit; the outer diameter of the second flexible portion being greater than the outer diameter of the portion having the maximum outer diameter of the first flexible portion.

A first endoscope system of the present invention is equipped with an endoscope having a distal end and a proximal end, and is provided with an insertion unit which can be inserted into a subject body, and an insertion assisting device which assists in insertion of the insertion unit into the subject body by being provided with an insertion hole capable of allowing passage therethrough of the insertion unit of the endoscope; the insertion unit being provided with a first flexible portion on a distal end and a second flexible portion that is provided at a site farther towards the proximal end than the first flexible portion and having an outer diameter larger than a site having the maximum outer diameter of the first flexible portion; and, the inner diameter of a distal opening of the insertion hole of the insertion assisting device being substantially equal to the outer diameter of the second flexible portion of the insertion unit.

A second endoscope system of the present invention is equipped with an insertion unit, extending from a control unit, which is inserted into a body cavity and which has a substantially tube-shaped first flexible portion on a distal end and a substantially tube-shaped second flexible portion on a proximal end; and a substantially tube-shaped endoscope insertion assisting device into which the insertion unit is inserted; the outer diameter of the second flexible portion being larger than the outer diameter of a portion having the maximum outer diameter of the first flexible portion; and the inner diameter of an opening in the distal end of the endoscope insertion assisting unit being roughly equal to the outer diameter of the second flexible portion.

DETAILED DESCRIPTION OF THE PREFERRED EMBODIMENT(S)

Figure 1:
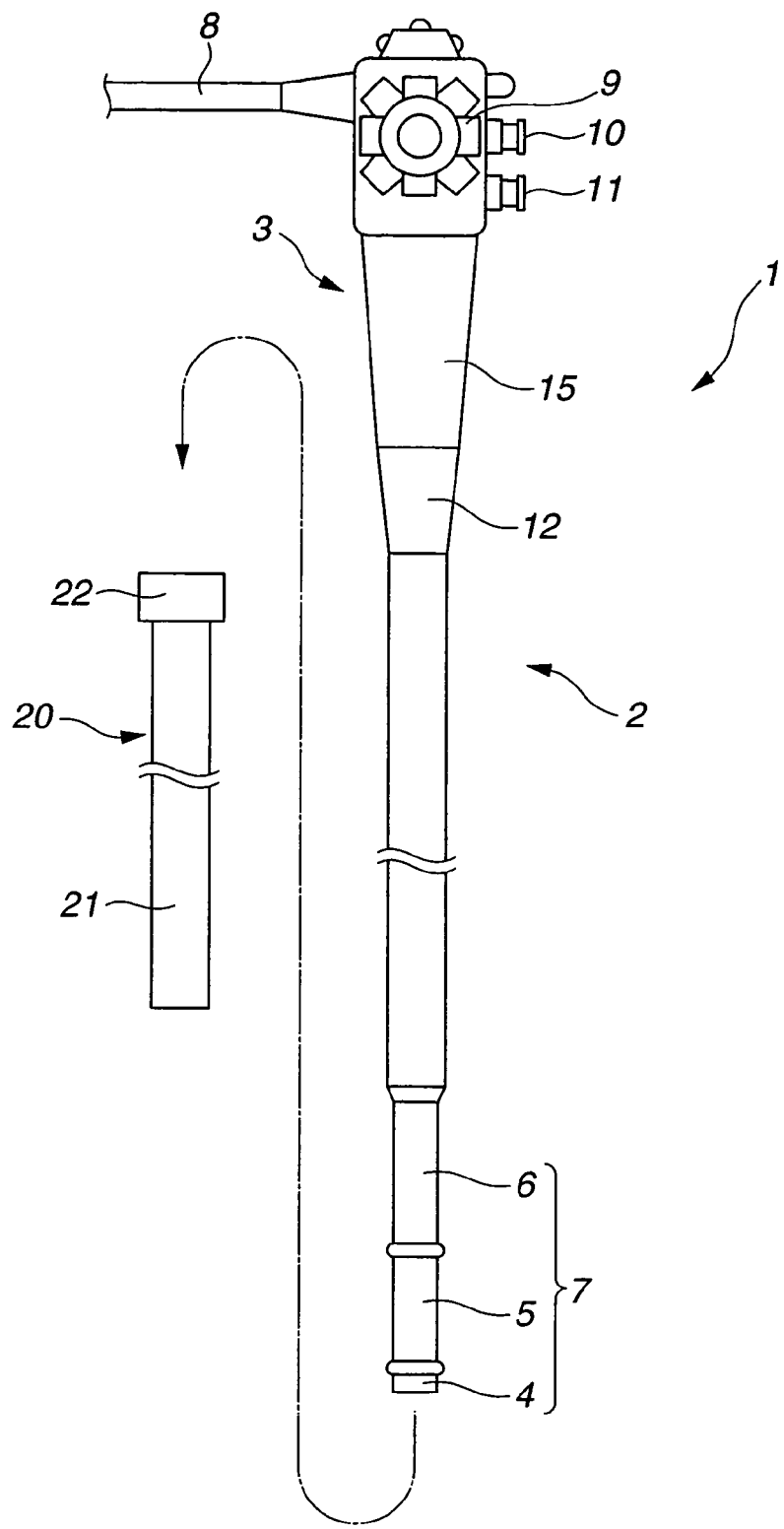
FIG. 1 is a drawing for explaining an endoscope system configuration as claimed in an embodiment of the present invention.
Figure 2:
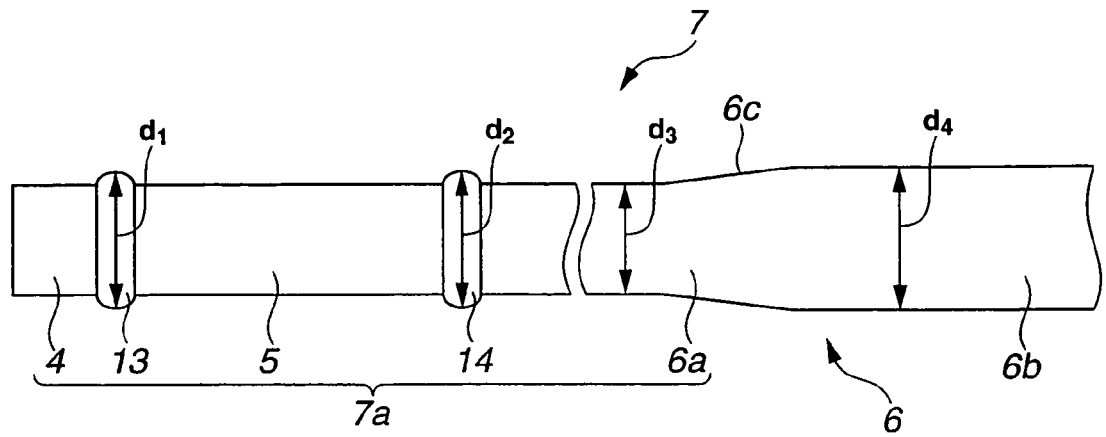
FIG. 2 is a drawing for explaining an insertion unit of an endoscope.
Figure 3:
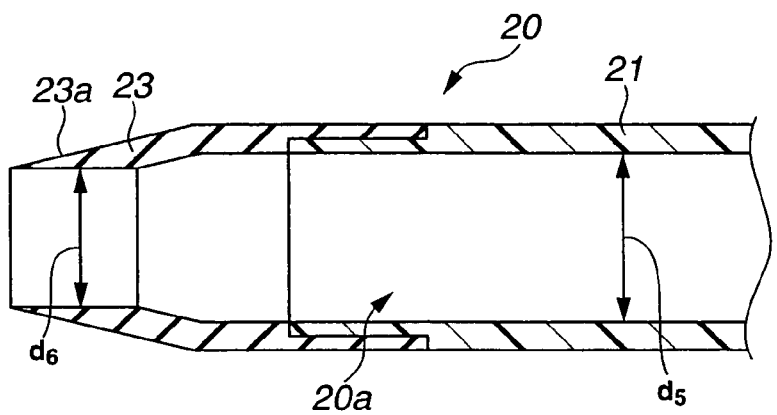
FIG. 3 is a cross-sectional view of a distal end obtained by severing an endoscope overtube in the lengthwise direction.
Figure 4:
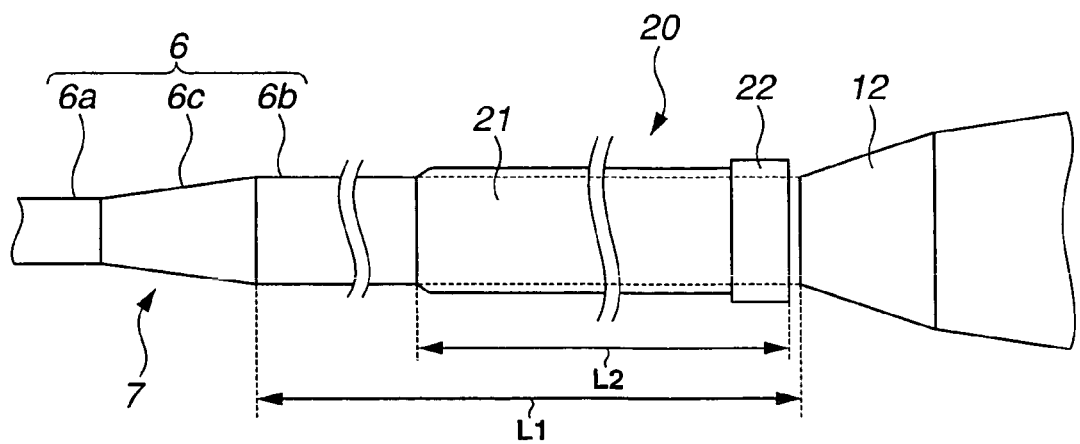
FIG. 4 is an explanatory drawing of the state in which an insertion unit of an endoscope is inserted into an endoscope overtube.

The following provides an explanation of the configuration of an endoscope system 1 of an embodiment of the present invention with reference to FIGS. 1 to 4. FIG. 1 is a drawing for explaining the configuration of the endoscope system 1 according to the present embodiment. FIG. 2 is a drawing for explaining an insertion unit 7 of an endoscope 2. FIG. 3 is a cross-sectional view of the distal end of an endoscope overtube 20 severed in the lengthwise direction. FIG. 4 is an explanatory drawing of the state in which the insertion unit 7 of the endoscope 2 is inserted into an endoscope overtube 20.

As shown in FIG. 1, the endoscope system 1 of the present embodiment is mainly comprised of the endoscope 2 and an endoscope insertion assisting device in the form of the endoscope overtube (to be simply referred to as the overtube) 20.

The endoscope 2 is mainly comprised of the insertion unit 7 inserted into the large intestine or other body cavity, a control unit 3 from which this insertion unit 7 extends, and a universal cord 8 extending from the side of this control unit 3. The insertion unit 7 of the endoscope 2 is comprised of, moving in order starting from the distal end, a rigid distal end 4, a bending portion 5 capable of bending this distal end 4 in any desired direction, and a flexible tube 6 having flexibility. An observation optical system, illumination optical system and so on not shown is arranged on the distal end 4 of the endoscope 2.

A bending control knob 9 for controlling bending of the bending portion 5, an air/water feed button 10, and a suction button 11 are arranged on a side of the control unit 3. In addition, the control unit 3 has an immobilizer 12 from which the flexible tube 6 of the insertion unit 7 extends, and a grip 15 for gripping by the physician. An electrical connector not shown is provided on the proximal end of the universal cord 8 which is removably connected to external devices in the form of a light source apparatus (not shown) and a processor (not shown).

As shown in FIG. 1, the endoscope insertion assisting device in the form of the overtube 20 is comprised of a roughly tube-shaped insertion tube 21 having low flexibility, and a roughly ring-shaped overtube grip 22 arranged on the proximal end of this insertion tube 21.

The following provides a detailed explanation of the insertion unit 7 of the endoscope 2 with reference to FIG. 2.

As shown in FIG. 2, the insertion unit 7 of the endoscope 2 is comprised of a roughly tube-shaped first flexible portion 7a on the distal end thereof, and a roughly tube-shaped second flexible portion (also expressed as the second flexible portion) 6b on the proximal end thereof.

The first flexible portion 7a is comprised of a distal end 4, a bending portion 5 and a first flexible tube 6a to be described later, in that order from the distal end side. A distal coupling 13, which serves as a connection between the distal end 4 and the bending portion 5, is provided on the distal end of this first flexible portion 7a, while a proximal coupling 14, which serves as a connection between the bending portion 5 and the flexible tube 6, is provided on the proximal end. This distal coupling 13 has an outer diameter d1 larger than the distal end 4 and the bending portion 5, and couples the distal end 4 and the bending portion 5 so as to maintain a predetermined connection strength. In addition, the proximal coupling 14 has an outer diameter d2 larger than the flexible tube 6a, which is described later, of the bending portion 5 and the flexible tube 6, and couples the bending portion 5 and the flexible tube 6 so as to maintain a predetermined connection strength.

As shown in FIG. 2, the diameter of the flexible tube 6 of the endoscope 2 increases in two stages moving from the distal end to the proximal end. In other words, the flexible tube 6 of the endoscope 2 is roughly in the shape of a tube in which the thickness is changed in two stages, having a narrow diameter on the distal end and a wide diameter on the proximal end, and having a portion of the first flexible portion 7a in the form of a first flexible tube portion (to be referred to as a narrow diameter flexible tube portion) 6a at the narrow diameter portion on the distal end, and the second flexible portion in the form of a second flexible tube portion (to be referred to as a large diameter flexible tube portion) 6b at the large diameter portion on the proximal end.

The narrow diameter flexible tube portion 6a has roughly the shape of a tube having a constant outer diameter d3 over roughly its entire length. In addition, the large diameter flexible tube portion 6b has roughly the shape of a tube having a constant outer diameter d4 which is larger than the outer diameter d3 of the narrow diameter flexible tube portion 6a over roughly its entire length (d3<d4). In addition, the flexible tube 6 of the endoscope 2 has a tapered surface 6c formed to have a tapered shape so that the outer periphery of the boundary between the narrow diameter flexible tube portion 6a and the large diameter flexible tube portion 6b forms a gentle slope.

The narrow diameter flexible tube portion 6a serving as the distal portion of the flexible tube 6 of the endoscope 2 is formed to have an outer sheath which is thinner than that of the large diameter flexible tube portion 6b serving as the proximal portion of the flexible tube 6, and is also designed to have a higher flexibility than the large diameter flexible tube portion 6b. In other words, the distal portion of the flexible tube 6 has high elasticity, while the proximal portion has low flexibility.

Furthermore, in the present embodiment, having low flexibility means that the rigidity of the large diameter flexible tube portion 6b of the flexible tube 6 of the insertion unit 7 is higher than that of the narrow diameter flexible tube portion 6a, namely that it is more resistant to bending. On the other hand, having high flexibility means that the rigidity of the narrow diameter flexible tube portion 6a of the flexible tube 6 of the insertion unit 7 is lower than that of the large diameter flexible tube portion 6b and is bent easily.

In addition, the outer diameter d4 of the large diameter flexible tube portion 6b of the endoscope 2 is equal to or greater than the outer diameter d1 of the distal coupling 13 and the outer diameter d2 of the proximal coupling 14 (d1≦d4, d2≦d4). Namely, the outer periphery of the large diameter flexible tube portion 6b of the flexible tube 6 of the endoscope 2 is the portion of maximum outer diameter of the insertion unit 7. In other words, the outer diameter d4 of the second flexible portion in the form of the large diameter flexible tube portion 6b of the insertion unit 7 is equal to or greater than the outer diameter of the insertion unit 7 more distal than the flexible tube 6, namely the outer diameter of the largest outer periphery of the first flexible portion 7a.

The following provides a detailed explanation of the overtube 20 with reference to FIG. 3.

As shown in FIG. 3, the overtube 20 is provided with a roughly ring-shaped seal 23 made of an elastic body such as rubber on the distal portion of the insertion tube 21, and is roughly in the shape of a tube made of a synthetic resin, for example, having a predetermined flexibility. This overtube 20 has an insertion hole 20a through which the insertion unit 7 of the endoscope 2 passes.

This insertion hole 20a of the overtube 20 has an inner diameter d5 slightly larger than the outer diameter d4 of the large diameter flexible tube portion 6b of the flexible tube 6 of the endoscope 2 (d4<d5). Furthermore, the inner diameter d5 of the insertion hole 20a may also be roughly equal to the outer diameter d4 of the large diameter flexible tube portion 6b of the flexible tube 6 of the endoscope 2 shown in FIG. 2 (d4≈d5).

An opening of the seal 23 of the overtube 20 has an inner diameter d6 equal to the outer diameter d4 of the large diameter flexible tube portion 6b of the flexible tube 6 (d4=d6). In other words, the overtube 20 has a minimum inner diameter at the opening of the seal 23 of the distal portion thereof. In addition, the outer periphery of the distal end of the seal 23 of the overtube 20 has a tapered surface 23a formed to have a tapered shape.

Furthermore, the inner diameter d6 of the opening of the seal 23 may also be an inner diameter d6 slightly smaller than the outer diameter d4 to a degree which allows the large diameter flexible tube portion 6b of the flexible tube 6 to pass through by utilizing the elastic deformation of the seal 23 (d4>d6). Moreover, the seal 23 of the overtube 20 is not limited to an elastic body, but rather may also be made of, for example, a synthetic resin.

Thus, the inner diameter d6 of the portion having the minimum narrow diameter of overtube 20 in the form of the opening on the distal end is equal to or greater than each of the outer diameter d1 of the distal coupling 13 of the endoscope 2 and the outer diameter d2 of the proximal coupling 14 (d1≦d6, d2≦d6).

In addition, as shown in FIG. 4, the overtube 20 has a shorter length in the lengthwise direction (total length) L2 than the length in the lengthwise direction (total length) L1 of the large diameter flexible tube portion 6b of the endoscope 2 (L1>L2).

Next, an explanation is provided of an endoscope examination of the large intestine using the endoscope system 1 comprised in this manner.

Figure 5:
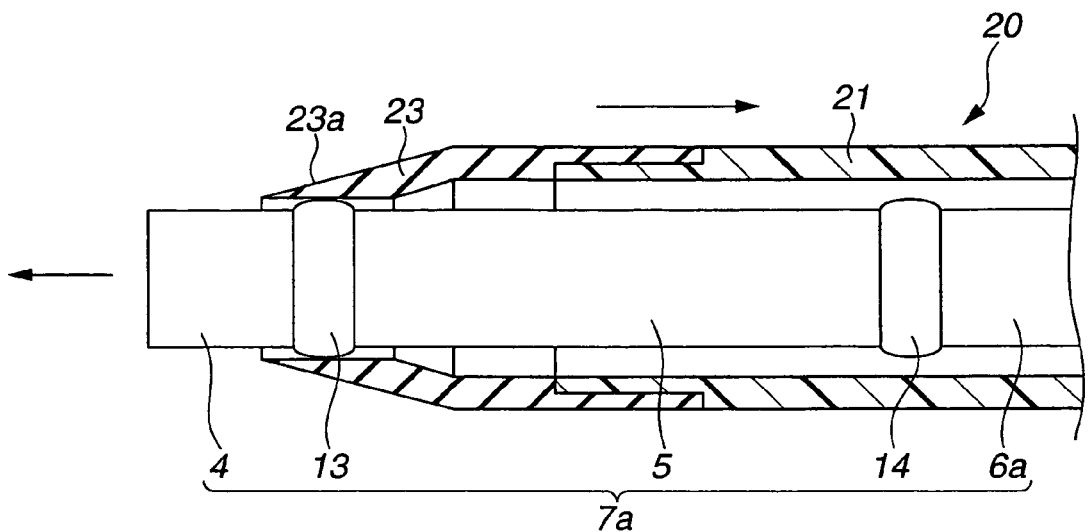
FIG. 5 is a partial cross-sectional view of the state in which a distal portion of an endoscope is inserted into an endoscope overtube.

First, prior to inserting the insertion unit 7 of the endoscope 2 into the large intestine of a patient, a physician inserts the insertion unit 7 of the endoscope 2 into the insertion hole 20a of the overtube 20 through the opening on the side of the overtube grip 22 thereof. As shown in FIG. 5, the physician passes the distal portion of the endoscope 2 through the opening in the distal end of the seal 23 of the overtube 20, and inserts the insertion unit 7 into the overtube 20.

At this time, since the respective outer diameters d1 and d2 of the outer periphery of distal coupling 13 and proximal coupling 14 of the endoscope are equal to or less than the inner diameter d6 of the portion having the minimum diameter of the overtube 20, the distal coupling 13 and the proximal coupling 14 are able to pass through the opening in the distal end of the overtube 20. Furthermore, FIG. 5 is a partial cross-sectional view of the state in which the distal portion of the endoscope 2 is inserted into the overtube 20.

As shown in FIG. 4, the physician inserts the insertion unit 7 of the endoscope 2 into the overtube 20 until the overtube grip 22 of the overtube 20 has reached the vicinity of the immobilizer 12 of the control unit 3 of the endoscope 2. While in this state, since the total length L2 of the overtube 20 is shorter than the total length L1 of the large diameter flexible tube portion 6b of the endoscope 2, the distal portion of the large diameter flexible tube portion 6b of the insertion unit 7 is not covered by the overtube 20.

Figure 6:
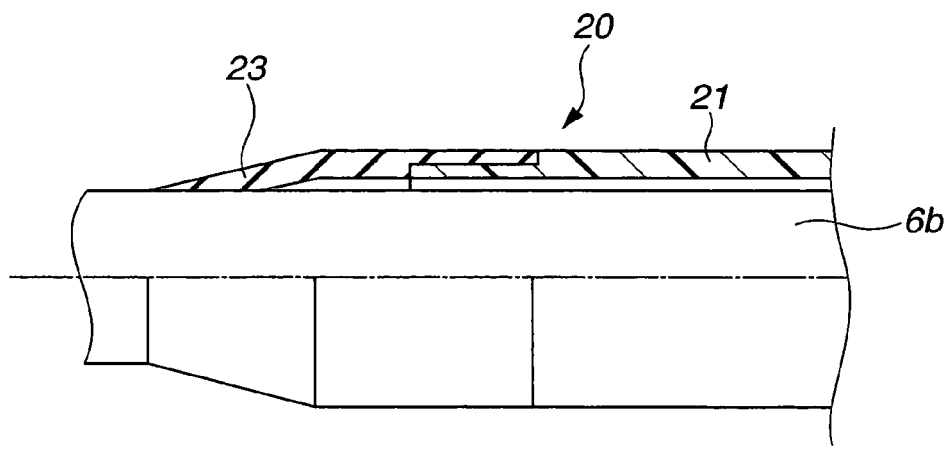
FIG. 6 is a partial cross-sectional view of the state in which an endoscope overtube is fit over a thick flexible tube of an endoscope.

In addition, as shown in FIG. 6, since the inner diameter of the opening of the seal 23 and the outer diameter of the large diameter flexible tube portion 6b are equal, the inner peripheral surface of the opening in the distal end of the seal 23 of the overtube 20 and the outer peripheral surface of the large diameter flexible tube portion 6b of the endoscope 2 are closely adhered. Moreover, as shown in FIG. 6, there is a slight gap between the outer peripheral surface of the large diameter flexible tube portion 6b of the endoscope 2 and the inner peripheral surface of the overtube 20.

Consequently, the physician slides the overtube 20 within the range of the total length of the large diameter flexible tube portion 6b of the insertion unit 7 of the endoscope 2 while maintaining a closely adhered state between the inner peripheral surface of the opening in the distal end of the seal 23 of the overtube 20 and the outer peripheral surface of the large diameter flexible tube portion 6b of the endoscope 2.

In other words, overtube 20 is slid within the range of the length (L1-L2) of the portion of the large diameter flexible tube portion 6b of the endoscope 2 not covered by the overtube 20 while maintaining a tightly adhered state between the inner peripheral surface of the opening in the distal end of the seal 23 and the outer peripheral surface of the large diameter flexible tube portion 6b of the endoscope 2. At this time, the inner peripheral surface of the opening in the distal end of the seal 23 of the overtube 20 is constantly tightly adhered to the outer peripheral surface of the large diameter flexible tube portion 6b of the endoscope 2.

Furthermore, FIG. 6 is a partial cross-sectional view of the state in which the overtube 20 is fit over the large diameter flexible tube portion 6b of the endoscope 2.

Next, the physician inserts the insertion unit 7 of the endoscope 2 over which the overtube 20 is fit into the large intestine from the distal end 4 thereof.

The physician aligns the endoscope 2 with a curved section of the large intestine and operates the bending control knob 9 of the control unit 3 of the endoscope 2. The physician then aligns the distal end 4 in a desired direction and inserts the insertion unit 7 in the direction of a deeper section of the large intestine while controlling bending of the bending section 5 of the endoscope 2. At this time, since the narrow diameter flexible tube portion 6a of the flexible tube 6 has high flexibility, the insertion unit 7 of the endoscope 2 is inserted by aligning with a curved section such as the sigmoid colon as a result of the narrow diameter flexible tube portion 6a following the curvature of the bending section 5.

After this narrow diameter flexible tube portion 6a of the flexible tube 6 has passed a curved section such as the sigmoid colon, the physician inserts the insertion unit 7 of the endoscope 2 in the direction of a deeper section of the large intestine by suitably bending and extending the large intestine while sliding the overtube 20 within the range over the large diameter flexible tube portion 6b. In addition, the physician inserts the insertion unit 7 in the direction of a deeper section of the large intestine while twisting and controlling the insertion unit 7 by gripping the large diameter flexible tube portion 6b of the endoscope 2.

At this time, the seal 23 of the distal portion of the overtube 20 maintains a state which constantly closely adheres the inner peripheral surface of the opening on the distal end to the outer peripheral surface of the large diameter flexible tube portion 6b of the endoscope 2 even during the time the overtube 20 is being slid. Moreover, the overtube 20 suppresses force which tends to contract the large intestine due to a predetermined flexibility thereof, thereby securing an insertion path for the large diameter flexible tube portion 6b of the endoscope 2.

In this manner, the physician inserts the insertion unit 7 of the endoscope 2 into a deeper section of the large intestine while controlling the bending of the bending section 5 and sliding the overtube 20 within the range over the large diameter flexible tube portion 6b of the flexible tube 6. Moreover, the physician is able to allow the distal end 4 to reach a deep section of the large intestine such as the vicinity of the appendix while controlling the twisting of the insertion unit 7 and so on by gripping the large diameter flexible tube portion 6b of the endoscope 2.

Next, the physician performs an endoscope examination of the large intestine while gradually retracting the insertion unit 7 of the endoscope 2 from the vicinity of the appendix towards the anus. During retraction of the insertion unit 7 of the endoscope 2 as well, the physician performs the endoscope examination of the large intestine while collectively retracting the overtube 20 and the insertion unit 7 while maintaining a state in which the overtube 20 is fit over the large diameter flexible tube portion 6b of the flexible tube 6. The physician then retracts the insertion unit 7 of the endoscope 2 together with the overtube 20 from the body cavity of the patient after having observed and treated examined sites.

As a result of the above procedure, during the endoscope examination of the body cavity such as the large intestine combining the use of the endoscope 2 and the overtube 20 serving as the endoscope system 1 of the present embodiment, since the outer peripheral surface of the large diameter flexible tube portion 6b of the flexible tube 6 of the endoscope 2 and the inner peripheral surface of the opening of the seal 23 at the distal portion of the overtube 20 are constantly tightly adhered, fecal matter in the large intestine does not enter the gap between the inner peripheral surface of the overtube 20 and the outer peripheral surface of the large diameter flexible tube portion 6b. In other words, fecal matter in the large intestine is prevented from entering the gap between the inner peripheral surface of the overtube 20 and the outer peripheral surface of the large diameter flexible tube portion 6b. Thus, fecal matter in the large intestine is prevented from entering the overtube 20.

As a result, fecal matter in the large intestine is prevented from traveling through the gap between the inner peripheral surface of the overtube 20 and the outer peripheral surface of the large diameter flexible tube portion 6b of the endoscope 2 and flowing out from the opening of the overtube grip 22 of the overtube 20. Thus, dissipation of fecal matter into the examination room is prevented.

In addition, the insertion unit 7 of the endoscope 2 improves ease of insertion into curved sections of the large intestine by facilitating controlling the bending of the bending section 5 so as to follow the curved sections of the large intestine as a result of the distal portion thereof having a high degree of flexibility, namely due to a portion of the easily bent first flexible portion 7a in the form of the narrow diameter flexible tube portion 6a. Moreover, the insertion unit 7 of the endoscope 2 is resistant to the effect of action which tends to contract the large intestine due to the low flexibility of the proximal portion thereof, namely the second flexible portion resistant to bending in the form of the large diameter flexible tube portion 6b. Consequently, a physician is able to easily insert the insertion unit 7 of the endoscope 2 into the large intestine.

Moreover, since the large diameter flexible tube portion 6b of the endoscope 2 has a large diameter, thereby allowing the large diameter flexible tube portion 6b to be gripped easily, the procedures of controlling twisting and controlling insertion for inserting the insertion unit 7 in the large intestine can be carried out easily.

Figure 7:
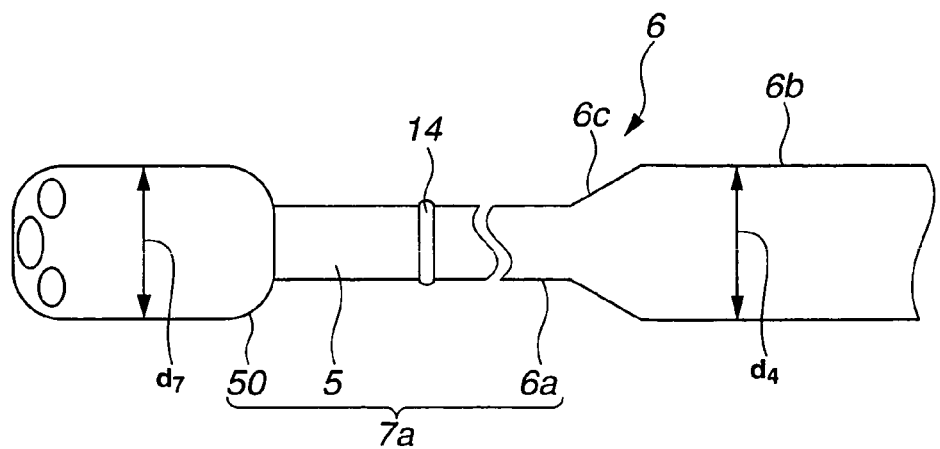
FIG. 7 is a drawing for explaining a variation of an endoscope provided with a capsule endoscope instead of a distal end on a distal portion of an insertion unit.

Furthermore, as shown in FIG. 7, a capsule endoscope 50 may be provided on the distal portion of the insertion unit 7 instead of the distal end 4. In other words, the first flexible portion 7a is comprised of, moving in order starting from the distal end, the capsule endoscope 50, the bending section 5 and the narrow diameter flexible tube portion 6a. In this case, the maximum outer diameter of the portion of the insertion unit 7 farther towards the distal end than the narrow diameter flexible tube portion 6a of the flexible tube 6 is the outer diameter d7 of the capsule endoscope 50.

Consequently, the outer diameter d4 of the second flexible portion of the insertion unit 7 in the form of the large diameter flexible tube portion 6b is equal to or greater than the outer diameter d7 of the capsule endoscope 50 ($d7 \leq d4$). In other words, since the outer periphery of the large diameter flexible tube portion 6b of the endoscope 2 has an outer diameter d4 equal to or greater than the outer diameter of the insertion unit 7 more distal than the flexible tube 6, namely the outer diameter of the largest outer periphery of the first flexible portion 7a, it is the portion of maximum diameter of the insertion unit 7.

In addition, as was previously stated, the opening of the seal 23 of overtube 20 has the inner diameter d6 equal to the outer diameter d4 of the large diameter flexible tube portion 6b of the flexible tube 6 ($d4=d6$). Thus, effects similar to the above-mentioned first embodiment are obtained even in the case of the endoscope 2 provided with the capsule endoscope 50 instead of the distal end 4 in the distal portion of the insertion unit 7.

Furthermore, the present invention is not limited to the above-described embodiment, and various modification and variations may be made without departing from the spirit or scope of the present invention.

What is claimed is:
1. An endoscope system comprising:
an endoscope provided with an insertion unit,
the insertion unit including:
a first flexible portion arranged on a distal end of the endoscope insertion unit; and
a second flexible portion coupled to a proximal end of the first flexible portion and having, over substantially an entire length thereof in a longitudinal direction, a constant outer diameter larger than a maximum outer diameter of the first flexible portion; and
an insertion assisting device including:
a roughly tube-shaped insertion tube having a low flexibility and an insertion hole formed from a proximal end to a distal end of the roughly tube-shaped insertion tube; and
a roughly ring-shaped seal made of an elastic body, a proximal end of the seal being coupled to a distal end of the insertion tube, the proximal end of the seal having an outer diameter equal to the outer diameter of the insertion tube and having an inner diameter equal to the inner diameter of the insertion tube so as to be smoothly continuous with the distal end of the insertion tube, the seal including on a distal end thereof an opening whose inner diameter is equal to or slightly smaller than the outer diameter of the second flexible portion of the insertion unit of the endoscope, the opening being configured so as to provide sealing with respect to an outer periphery of the second flexible portion.

2. The endoscope system according to claim 1, wherein the seal has a tapered surface on a distal end outer periphery thereof.

3. The endoscope system according to claim 1, wherein the inner diameter of the opening of the seal configures a minimum inner diameter of the insertion assisting device.

4. The endoscope system according to claim 2, wherein the inner diameter of the opening of the seal configures a minimum inner diameter of the insertion assisting device.

5. The endoscope system according to claim 1, wherein the outer diameter of the second flexible portion of the insertion unit of the endoscope is equal to a maximum outer diameter of the insertion unit of the endoscope.

6. The endoscope system according to claim 2, wherein the outer diameter of the second flexible portion of the insertion unit of the endoscope is equal to a maximum outer diameter of the insertion unit of the endoscope.

7. The endoscope system according to claim 3, wherein the outer diameter of the second flexible portion of the insertion unit of the endoscope is equal to a maximum outer diameter of the insertion unit of the endoscope.

8. The endoscope system according to claim 4, wherein the outer diameter of the second flexible portion of the insertion unit of the endoscope is equal to a maximum outer diameter of the insertion unit of the endoscope.

9. The endoscope system according to claim 1, wherein the second flexible portion of the insertion unit of the endoscope is longer than an entire length of the insertion assisting device.

10. The endoscope system according to claim 2, wherein the second flexible portion of the insertion unit of the endoscope is longer than an entire length of the insertion assisting device.

11. The endoscope system according to claim 3, wherein the second flexible portion of the insertion unit of the endoscope is longer than an entire length of the insertion assisting device.

12. The endoscope system according to claim 4, wherein the second flexible portion of the insertion unit of the endoscope is longer than an entire length of the insertion assisting device.

* * * * *